(12) United States Patent
Gao

(10) Patent No.: US 8,601,923 B1
(45) Date of Patent: Dec. 10, 2013

(54) ROD CUTTER WITH EXCHANGEABLE CUTTERS

(75) Inventor: Hua Gao, Fox Point, WI (US)

(73) Assignee: Bradshaw Medical, Inc., Kenosha, WI (US)

(*) Notice: Subject to any disclaimer, the term of this patent is extended or adjusted under 35 U.S.C. 154(b) by 280 days.

(21) Appl. No.: 12/925,757

(22) Filed: Oct. 29, 2010

(51) Int. Cl.
*B26D 1/03* (2006.01)

(52) U.S. Cl.
USPC .................... 83/199; 83/196; 30/92

(58) Field of Classification Search
USPC .............. 83/198–200; 30/103–108, 173
See application file for complete search history.

(56) References Cited

U.S. PATENT DOCUMENTS

| | | | | |
|---|---|---|---|---|
| 54,520 A * | 5/1866 | Flinn | | 30/226 |
| 327,610 A * | 10/1885 | Stackpole | | 83/199 |
| 534,265 A * | 2/1895 | Hogg | | 83/199 |
| 596,837 A * | 1/1898 | Werner | | 83/199 |
| 649,850 A * | 5/1900 | Levalley | | 83/199 |
| 1,265,345 A * | 5/1918 | La Rock | | 83/200 |
| 2,385,835 A * | 10/1945 | Neal | | 30/250 |
| 2,638,985 A * | 5/1953 | Ross | | 225/96 |
| 2,649,913 A * | 8/1953 | Linder | | 83/200 |
| 2,915,820 A * | 12/1959 | Naito | | 30/227 |
| 3,315,669 A | 4/1967 | Rhodes | | |
| 3,621,745 A * | 11/1971 | Cavalan | | 83/198 |
| 3,665,604 A * | 5/1972 | Kowal | | 30/102 |
| 4,581,958 A | 4/1986 | Shull | | |
| 5,261,303 A * | 11/1993 | Strippgen | | 83/199 |
| 5,285,702 A | 2/1994 | Hillinger | | |
| 5,363,711 A * | 11/1994 | Seto | | 74/25 |
| 5,404,616 A | 4/1995 | Carmien | | |
| 5,515,574 A | 5/1996 | Larson | | |
| 5,836,937 A | 11/1998 | Holmes | | |
| 5,988,027 A * | 11/1999 | Lenox | | 83/13 |
| 6,058,820 A * | 5/2000 | Rinner | | 83/200 |
| 6,238,292 B1 | 5/2001 | Pelkey | | |
| 6,840,146 B2 * | 1/2005 | Gosis et al. | | 83/199 |
| 8,127,454 B1 * | 3/2012 | Gao | | 30/92 |
| 2003/0200849 A1 * | 10/2003 | Kochi | | 83/199 |
| 2008/0000091 A1 * | 1/2008 | Eriguchi | | 30/90.1 |

* cited by examiner

*Primary Examiner* — Andrea L Wellington
*Assistant Examiner* — Fernando Ayala
(74) *Attorney, Agent, or Firm* — Absolute Technology Law Group, LLC; Jill Gilbert Welytok

(57) ABSTRACT

A rod cutter having two cutters that are exchangeable and with one thereof being operatively stationary and the other being pivotally and with cutting edges therebetween. A cover extends over the cutters so that access to the cutters is available, and they can be interchanged in their installed positions to reposition the cutting edges exposed to the rod. A ball bearing supports the pivotal cutter and it has an axial restriction for rendering axial support to the pivotal cutter. The method of cutting with both radial and axial cutter support is described.

12 Claims, 6 Drawing Sheets

ROD CUTTER WITH EXCHANGEABLE CUTTERS

This invention relates to a rod cutter with exchangeable cutters, for use in the medical field. It is acknowledged that rod cutters are already known in the art.

The present invention improves upon the prior art by having replaceable cutters which are readily and easily replaced. This arrangement also provides for sturdy and accurate cutter mounting. The cutters can be replaced for reasons of wear or size of rod to be cut.

Also, the cutter can be hand held or table mounted for the rod cutting.

In accomplishing the above, this cutter is accurate for rod lengths cut, and it is clean cutting to present a cut rod without cut end distortion.

Still further, this cutter has a mechanical advantage in applying the force for cutting. Also it has means for adjusting the initial position of the cutters in preparing for cutting.

Still further, this cutter has means for aligning the cutter openings so that the rod can be inserted into the cutters readily and accurately in preparation for cutting.

The above features can be accomplished in an accurate and readily achievable manner.

Other objects and advantages will become known upon reference to the following description and its drawings.

DETAILED DESCRIPTION OF THE PREFERRED EMBODIMENT

Figure 1:
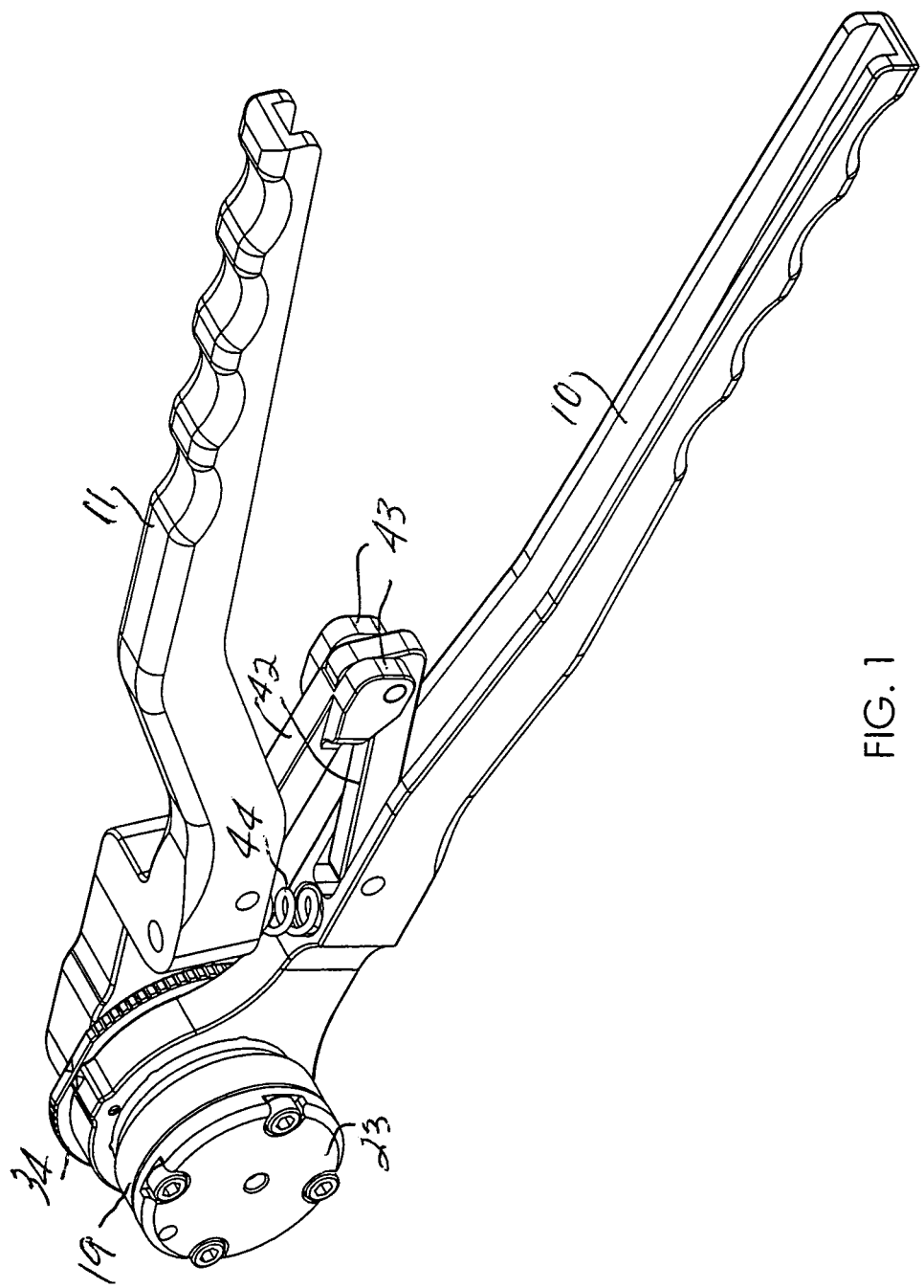
FIG. 1 is a rear perspective view of the assembled cutter of this invention.

As shown, this cutter has two handles 10 and 11 with handle 10 being stationary and handle 11 being pivotal. There are two hexagonally shaped cutters 12 and 13 respectively controlled by the handles 10 and 11 such that cutter 12 is fixed with handle 10, which serves as a base unit, while cutter 13 is pivotal with handle 11. The assembly extends along an axis A, and cutters 12 and 13 have radially offset respective and equal size cutter openings 14 and 16 which are available to receive the unshown rod to be cut. The radial offset relative to axis A is the same for both openings 14 and 16 so they axially align upon rotation of the handle for rotation of cutter 13. The eccentric openings have respective rod circular cutting edges 17 and 18 of the same diameter therearound and openings 14 and 16 also have rod cutting edges 17 and 18 at both limits ends of openings 14 and 16. Openings 14 and 16 also have rod cutting edges 17 and 18, and rotation of the cutter 13 about the axis A and relative to stationary cutter 12 causes the cutter opening 16 to orbit axis A so the rod is cut by edges 17 and 18.

It should be understood that the unshown rod to be cut has a diameter equal to that of the openings 14 and 16 for clean cutting. There is a tubular body piece 19 which has a hexagonal end 21 which fits snugly into an opening 22 in the handle 10 to be non-rotatable by engagement of hexagonal mating surfaces between the handle 10 and the body 19. A cover 23 has four screws 24 affixing it to the body 19, and it presents a hexagonal recess opening 26 for non-rotation reception of the cutter 12. There are only four cap screws 24 holding the cover 23 onto the handle, the cutters 12 and 13 are readily available and readily removed and replaceable when the cover is removed. Again, it will be noticed that the cutter 12 has a hexagonal exterior at 27, and the cutter fits non-rotationally into the hexagonal opening 26 in the cover 23 to be held non-rotationally. There is an eccentric hole 25 on the cover 23 in line with the holes 14 and 16 for reception of the rod to be cut. Also, the body and the cover have surfaces facing each other for contacting said cutters in the direction of the axis shown.

Figure 2:
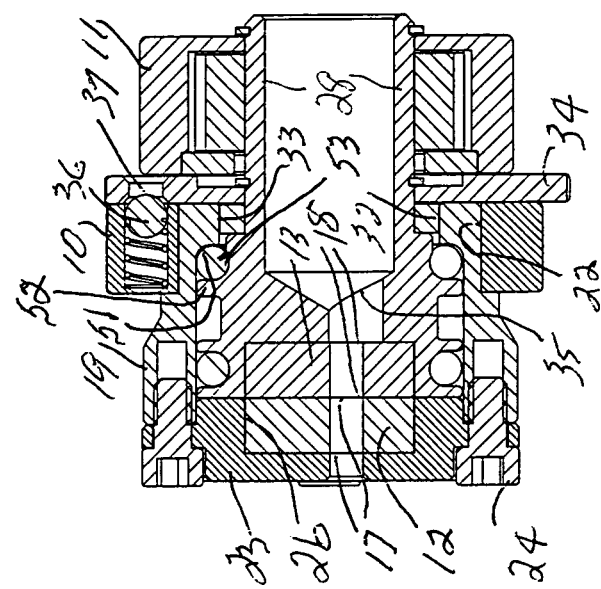
FIG. 2 is a section view of the cutter mechanism.
Figure 3:
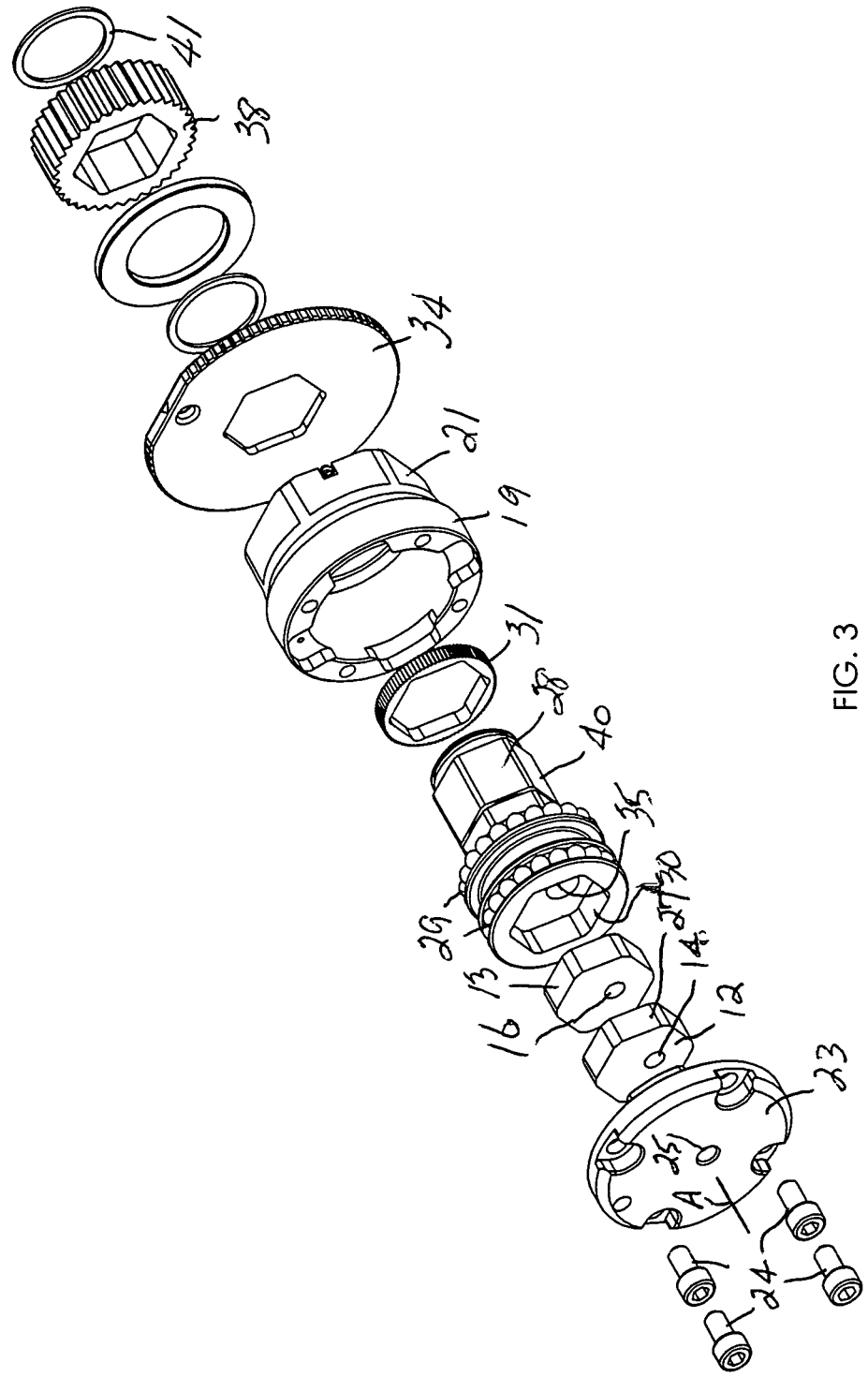
FIG. 3 is an exploded view of most of the cutter mechanism.
Figure 4:
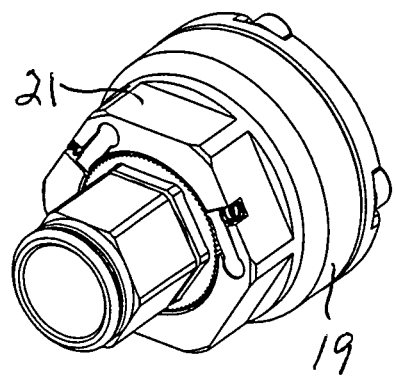
FIG. 4 is an assembled front perspective view of a portion of the mechanism.
Figure 5:
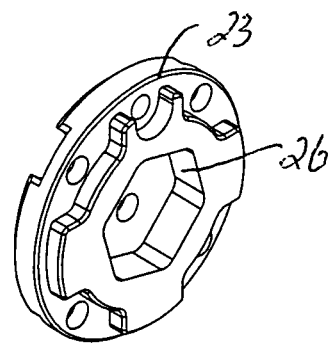
FIG. 5 is a rear perspective view of one part of the mechanism.

For the rotation of the cutter 13, there is the tubular body 28 extending into the body 19 with intervening ball bearings 29 for rotation of the body 28 in the body 19. Also, the body 28 has a hexagonal pocket 30 for snug reception of the cutter 13 which therefore rotates with the rotation of the body 28. The size of the openings 26 and 30 is to snugly receive the cutters, so the depth of the openings 26 and 30 is a blind opening and the thickness of each cutter. At times it is desired that the body 19 not rotate, such as when the cutter openings are to be aligned with each other for preparation for rod insertion and then cutting action, and to avoid the rotation tendency created by the overhanging handle 11, there is a dampener or brake 31 non-rotationally mounted on the body 28 with the hexagonal mating shown, and its circumference is in rubbing contact with the body 19, as seen in FIG. 2. The dampener is of a friction inducing material, and it has a friction braking circumference 32, with a tread thereon, in contact with the circular interior of the body 19 as at 33. So the rotated position of the cutter 13 can be manually controlled for the alignment desired.

A circular plate 34 is non-rotatably mounted on the polygonal end 28 of the body 19 and extends to the exposed radial exterior to be available for manual rotation to rotate the body 19 to a desired position for aligning the cutter openings 14 and 16. There is spring-urged ball detent 36 on the body 22 and it aligns with the opening 37 in the plate 34 and thereby establishes the rotated position of the cutter 13. All for aligning the cutters openings 14 and 16 in preparation for receiving the rod for cutting. The plate 34 is exposed to the exterior of the assembly for that rotation access by the operator's finger. Also, body 19 has a passageway 35 for reception of the rod in its alignment with the cutter openings.

Figure 6:
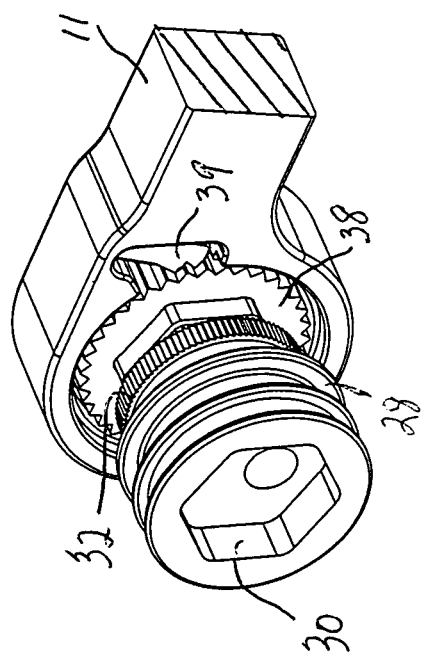
FIG. 6 is a rear perspective view of a portion of the mechanism.

For performing the cutting, the cutter 13 is rotated and that requires that the body 28 be rotated. A gear 38 is non-rotatably mounted on the rotatable body 28 which carries the cutter 13. The teeth of the gear are engaged by a pawl 39 carried by the handle 11 as seen in FIG. 6. The gear and the pawl thus rotate the body 19 for the cutting action. The pawl also acts as a ratchet in that the pawl will regress in rotated position after a cutting drive rotation is applied, so the ratchet action can continue through the full cut. A snap ring 41 secures the assembly axially.

FIGS. 2 and 6 show the handles wherein handle 11 carries the pawl 39 and surrounds the gear 38 which has its hexagonal opening receiving the mating end 40 of the body 28. There is a linkage at 42 in FIG. 1 and it is pinned between the two handles for handle control. Also, linkage restriction is at 43 and can hold the handles in their positions. A return spring 44 pushes on the handle 11 to return it to its up position.

Figure 7:
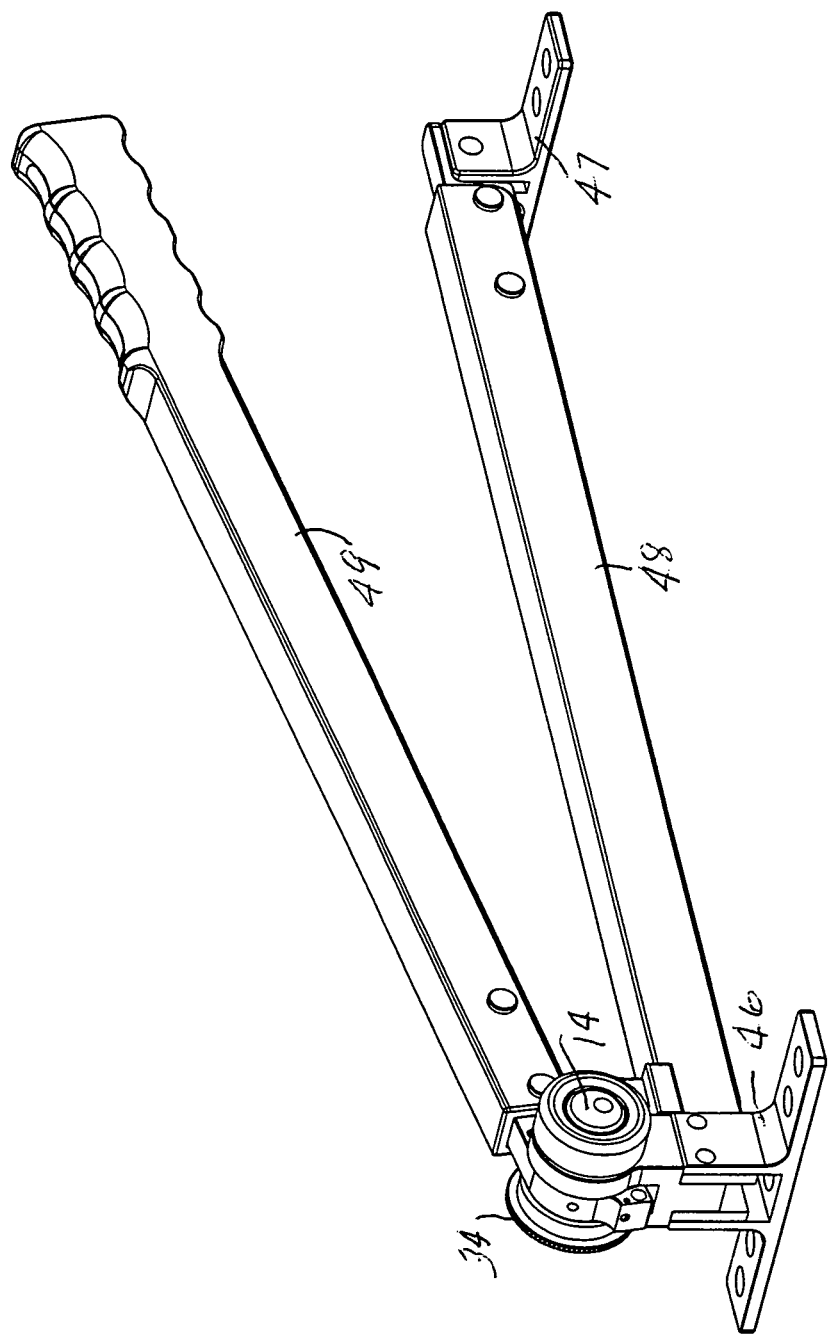
FIG. 7 is a front perspective view of the mechanism mounted on a pair of brackets for table mounting of the cutter.

FIG. 7 shows the cutter with table mountings 46 and 47 and a bar 48 therebetween. Then there is a handle 49 pivotal with the assembly just described, so all can be fixed and supported on a table for cutting.

Of course the shown hexagonal matings can be of other well known rotational connections, such as a spline or other polygonal shape. The body 19 and cover 23 present a base for the pivotal mounting of the body 28, and there is the pivoting handle 11 on the member 28. There can be an unshown set of pairs of additional cutters 12 and 13 and with the cutters in each pair being identical to each other and having matching openings 14 and 16 unique to each pair and different in diametrical size from the shown rod openings 14 and 16 to thereby accommodate different size rods by each pair. The cutter 12 can be inserted first, then the cutter 13, so different cutting edges 17 and 18 at the ends of the cutter openings are presented to the rod. The cutters are of identical size and shape including polygonal edge shape so they are interchangeable. Shapes other than hexagonal can be used for the non-rotation.

An important feature is shown in FIG. 2 with the showing of the ball bearing row on the right. Here it will be seen that the ball bearing provides both axial and radial support for the tubular piece 28. The arrangement is that the ball bearing row 29 on the right takes both the axial and radial loads during cutting action in the pivoting of the piece 28 and its cutter 13. That row of balls is trapped both radially and axially, and it resists the axially movement of the body 28 and the cutter 13 to the right, as they are seen in FIG. 2. That avoids the axial separation of the cutters 12 and 13 during the cutting loads.

The two tubular body pieces 19 and 28 have the right row of the ball bearing 29 therebetween. The piece 28 has a surface 51 extending adjacent the balls 29 in the right row and facing axially to trap the balls 29 in the axial direction and against the cutting force on the cutter 13 which is carried by the piece 28. In detail, the surfaces 51 are a quarter circle, as shown, and are to the sides of the balls away from the cutting edges 17 and 18. and there is the partition 52 facing the surface 51 and trapping the balls 53 therebetween, so the piece 28 cannot move in either axial direction. The surface 51 and partition 52 are axially spaced apart the diameter of one ball 29. So the body piece 19 is in a fixed position and it engages the balls 53 for both radial and axial support of the body 28, and thereby likewise supports the cutter 13.

As described above, the cutter presents a method of cutting while restraining the axial movement of the pivotal cutter 13, thereby assuring a clean and accurate cut of the rod. So the ball bearing presents both the radial and axial support for the moving cutter 13. The balls 53 are trapped by the stationary piece 19 through surface 51 and by the balls 53 on the partition 52, so the cutters do not move away from each other but yet the body 28 is pivotally supported for carrying the cutter 13.

So that row of balls 29 is axially engaged with both the races and 52, which are the outer and inner races, for axial supporting of the pivotal piece 28. That axial restraint resists the axial force applied on the piece 28 in the cutting action. So that row of balls 29 is arranged to take both radial and axial loads to stabilize the piece 28 and support the cutter 13. So the cutting action tends to move the cutter to the right, as viewed in FIG. 2, and the surface 51 restrains that force for axial movement.

What is claimed is:

1. A ball bearing rod cutter comprised of:
   two handles pivoted together along a pivot axis, and rod cutters on said handles for receiving a rod to be cut,
   each of said handles having a hexagonal recess with one or more hexagonal mating surfaces for receiving a hexagonal tubular body wherein said hexagonal recesses face each other,
   two hexagonal rod cutters disposed in each of said hexagonal recesses for the pivoting of one of each of said hexagonal cutters with the pivoting of one of said handles,
   wherein said hexagonal cutters each have an opening for receiving a rod extending in length parallel to said pivot axis and to be cut in length, and
   a cover removably mounted on each of said handles and extending over each of said cutters for removably securing said cutters on said handles,
   a hexagonal tubular body having an inner portion and an outer portion, wherein said outer portion includes two rows of ball bearings disposed around said perimeter of said inner portion to receive both axial and radial loads during cutting action to prevent said hexagonal cutters from being disengaged by axial force during the cutting motion and said inner portion includes an elongated hexagonal end portion,
   wherein said hexagonal tubular body is operatively coupled with a gear which rotates with the rotation of the body,
   wherein said hexagonal tubular body has a hexagonal pocket for snug reception of one of said cutters.

2. The rod cutter as claimed in claim 1, further comprising:
   a means for securing said cutters non-rotationally on said handles.

3. The rod cutter as claimed in claim 1,
   wherein said cover is releasably secured to said handles for retaining each of said cutters on said handles and for the movement of said cutters relative to said handles upon removal of each of said cover.

4. The rod cutter as claimed in claim 1, further including,
   a base,
   a handle pivotally mounted on said base,
   two rod cutters non-rotationally and removably supported on said base and with one of said cutters connected with said handle for pivoting therewith, and
   a cover removably attached to said base and extending over said cutters for releasably retaining said cutters on said base.

5. The rod cutter for use in the medical arts, as claimed in claim 1, further comprising:
   a plurality of cutters for interchanging said cutters on said base upon removal of said cover and with said cutters having circular cutting openings for receiving and cutting said rods of differing sizes.

6. The rod cutter for use in the medical arts, as claimed in claim 1 comprising:
   a base and said cover both presenting a wall to said cutters for restricting movement of said cutters toward said walls and with said walls facing each other, and
   said base and said cutters having mutually engaged surfaces for non-rotationally releasably holding said cutters on said base.

7. The rod cutter for use in the medical arts, as claimed in claim 1, further comprising:
   each said cutter having an opening therethrough for reception of a rod to be cut, and
   each said cutter having a rod cutting edge at both ends of said opening in said cutter for cutting at said ends upon reversing said cutters in said recesses.

8. The rod cutter as claimed in claim 1, further comprising:
a brake interposed between said base and said handle for retarding pivoting of said handle relative to said base.

9. The rod cutter as claimed in claim 1, further comprising:
a base,
a handle pivotal on said base,
a rod cutter on said handle for pivoting therewith, and
a pivot control member engaged with said handle for pivotally setting said cutter relative to said base.

10. The rod cutter as claimed in claim 1, further comprising:
a pivot control member engaged with said handle for pivotally setting said cutter relative to said base,
a second rod cutter removably mounted on said base, and
a pivot control member engaged with said handle for pivotally setting said first cutter relative to said base.

11. The rod cutter as claimed in claim 1, wherein said ball bearings are:
operative between said base piece and said body piece and said base piece and said body piece having axially facing surfaces with said ball bearings therebetween for axially restricting said body tubular body piece relative to said base piece, and
a handle connected with said second rod cutter and being pivotal about said axis on said body piece for pivoting said one cutter relative to said second cutter.

12. The rod cutter as claimed in claim 1 further comprising:
said row of ball bearings further including a row of spherical balls with each thereof having a diameter and being interposed between said surfaces,
said axially facing surfaces being axially spaced apart the distance of said diameter of each of said balls and being in rolling contact with said balls.

* * * * *